United States Patent
Amoro et al.

(10) Patent No.: US 11,839,688 B2
(45) Date of Patent: *Dec. 12, 2023

(54) APPARATUS AND METHOD FOR CRYOGRANULATING A PHARMACEUTICAL COMPOSITION

(71) Applicant: MannKind Corporation, Westlake Village, CA (US)

(72) Inventors: Edwin Amoro, West Haven, CT (US); Karel Vanackere, Knokke-Heist (BE); Michael A. White, Brookfield, CT (US)

(73) Assignee: MannKind Corporation, Westlake Village, CA (US)

( * ) Notice: Subject to any disclaimer, the term of this patent is extended or adjusted under 35 U.S.C. 154(b) by 237 days.

This patent is subject to a terminal disclaimer.

(21) Appl. No.: 17/363,162

(22) Filed: Jun. 30, 2021

(65) Prior Publication Data

US 2021/0322320 A1    Oct. 21, 2021

Related U.S. Application Data

(60) Continuation of application No. 16/675,471, filed on Nov. 6, 2019, now Pat. No. 11,077,063, which is a
(Continued)

(51) Int. Cl.
*A61K 9/16* (2006.01)
*A61J 3/00* (2006.01)
(Continued)

(52) U.S. Cl.
CPC ............ *A61K 9/1682* (2013.01); *A61J 3/00* (2013.01); *A61K 9/16* (2013.01); *A61K 9/1617* (2013.01); *A61K 38/28* (2013.01); *B01J 2/06* (2013.01)

(58) Field of Classification Search
CPC .. A61J 3/00; A61K 38/28; A61K 9/16; A61K 9/1617; A61K 9/1682; A61K 31/495;
(Continued)

(56) References Cited

U.S. PATENT DOCUMENTS

| | | |
|---|---|---|
| 3,228,838 A | 1/1966 | Rinfret et al. |
| 3,298,188 A | 1/1967 | Webster et al. |

(Continued)

FOREIGN PATENT DOCUMENTS

| | | |
|---|---|---|
| JP | 11-236336 A2 | 8/1999 |
| JP | 2009-507931 T2 | 2/2009 |

(Continued)

OTHER PUBLICATIONS

Russian Office Action dated Feb. 10, 2022, in connection with Russian Application No. 2017141631.
(Continued)

*Primary Examiner* — Savitha M Rao
(74) *Attorney, Agent, or Firm* — Wolf, Greenfield & Sacks, P.C.

(57) ABSTRACT

Cryogranulation systems with improved dispenser assemblies are provided for use in manufacturing frozen pellets of pharmaceutical substances in a fluid medium. Methods of cryogranulating the pharmaceutical substance in the fluid medium are also provided. In particular embodiments, the dispenser assembly is used with suspensions or slurries of pharmaceutical compositions including biodegradable substances, such as proteins, peptides, and nucleic acids. In certain embodiments, the pharmaceutical substance can be adsorbed to any pharmaceutically acceptable carrier particles suitable for making pharmaceutical powders. In one embodiment, the pharmaceutical carrier can be, for example, diketopiperazine-based microparticles. The dispenser assembly improves the physical characteristics of the
(Continued)

cryopellets formed and minimizes product loss during processing.

9 Claims, 7 Drawing Sheets

Related U.S. Application Data division of application No. 16/051,645, filed on Aug. 1, 2018, now Pat. No. 10,500,159, which is a continuation of application No. 15/407,375, filed on Jan. 17, 2017, now Pat. No. 10,052,285, which is a division of application No. 14/065,609, filed on Oct. 29, 2013, now Pat. No. 9,566,243, which is a continuation of application No. 12/917,623, filed on Nov. 2, 2010, now Pat. No. 8,590,320.

(60) Provisional application No. 61/257,385, filed on Nov. 2, 2009.

(51) Int. Cl.
*B01J 2/06* (2006.01)
*A61K 38/28* (2006.01)

(58) Field of Classification Search
CPC .......... A61K 39/00; A61K 8/26; A61K 8/342; A61K 8/347; A61K 8/494; B01J 2/06; B01J 19/24; B01J 19/2415; A61Q 15/00; B65B 1/366; B65B 37/12; C07D 241/08
See application file for complete search history.

(56) References Cited

U.S. PATENT DOCUMENTS

| | | | |
|---|---|---|---|
| 4,479,363 A | 10/1984 | Gibson et al. | |
| 4,552,681 A | 11/1985 | Koch et al. | |
| 4,655,047 A | 4/1987 | Temple et al. | |
| 4,843,840 A | 7/1989 | Gibson | |
| 4,982,577 A | 1/1991 | Milankov et al. | |
| 5,096,746 A | 3/1992 | Strizki | |
| 5,352,461 A | 10/1994 | Feldstein et al. | |
| 5,401,502 A | 3/1995 | Wunderlich et al. | |
| 5,405,616 A | 4/1995 | Wunderlich et al. | |
| 5,503,852 A | 4/1996 | Steiner et al. | |
| 5,522,227 A | 6/1996 | Appolonia | |
| 5,881,561 A | 3/1999 | Viard | |
| 6,071,497 A | 6/2000 | Steiner et al. | |
| 6,216,470 B1 | 4/2001 | Kosock et al. | |
| 6,331,318 B1 | 12/2001 | Milstein | |
| 6,444,226 B1 | 9/2002 | Steiner et al. | |
| 6,652,885 B2 | 11/2003 | Steiner et al. | |
| 6,770,300 B1 | 8/2004 | Hoffman et al. | |
| 6,815,533 B1 | 11/2004 | Baker et al. | |
| 7,062,924 B2 | 6/2006 | Irvine et al. | |
| 7,475,554 B2 | 1/2009 | Irvine et al. | |
| 7,648,960 B2 | 1/2010 | Steiner et al. | |
| 7,943,572 B2 | 5/2011 | Cheatham et al. | |
| 8,590,320 B2 | 11/2013 | Amoro et al. | |
| 9,566,243 B2 | 2/2017 | Amoro et al. | |
| 10,052,285 B2 | 8/2018 | Amoro et al. | |
| 10,500,159 B2 | 12/2019 | Amoro et al. | |
| 11,077,063 B2 | 8/2021 | Amoro et al. | |
| 2004/0018152 A1 | 1/2004 | Steiner et al. | |
| 2005/0008754 A1 | 1/2005 | Sweeney et al. | |
| 2005/0232930 A1 | 10/2005 | Richter-Friss et al. | |
| 2007/0051117 A1 | 3/2007 | Irvine et al. | |
| 2007/0196503 A1 | 8/2007 | Wilson et al. | |
| 2008/0060213 A1 | 3/2008 | Gehrmann et al. | |
| 2008/0260838 A1 | 10/2008 | Hokenson et al. | |
| 2009/0110647 A1 | 4/2009 | Richardson et al. | |
| 2009/0111749 A1 | 4/2009 | Richardson et al. | |
| 2011/0100028 A1 | 5/2011 | Amoro et al. | |
| 2014/0044790 A1 | 2/2014 | Amoro et al. | |
| 2017/0119673 A1 | 5/2017 | Amoro et al. | |
| 2018/0338920 A1 | 11/2018 | Amoro et al. | |
| 2020/0069590 A1 | 3/2020 | Amoro et al. | |

FOREIGN PATENT DOCUMENTS

| | | |
|---|---|---|
| RU | 2248790 C2 | 3/2005 |
| RU | 256122 C2 | 9/2015 |
| SU | 1669730 A1 | 8/1991 |
| WO | WO 00/06179 A1 | 2/2000 |
| WO | WO 03/020959 A1 | 3/2003 |
| WO | WO 03/028486 A2 | 4/2003 |
| WO | WO 2005/058474 A1 | 6/2005 |
| WO | WO 2007/057888 A2 | 5/2007 |
| WO | WO 2007/098500 A2 | 8/2007 |
| WO | WO 2009/055740 A2 | 4/2009 |
| WO | WO 2009/055742 A1 | 4/2009 |
| WO | WO 2010/003430 A1 | 1/2010 |
| WO | WO 2011/053959 A1 | 5/2011 |

OTHER PUBLICATIONS

International Search Report and Written Opinion dated Jan. 10, 2011 from International Application No. PCT/US2010/055085.
Extended European Search Report dated Feb. 28, 2013 from European Application No. 10827637.9.
Extended European Search Report dated Jul. 2, 2019 in connection with European Application No. 18215323.9.
Australian Examination Report dated Apr. 21, 2016 from Australian Application No. AU 2015201885.
Chinese Office Action dated Sep. 19, 2016 from Chinese Application No. 201410219078.2.
Japanese Office Action dated Aug. 24, 2016 from Japanese Application No. 2015-202462.
Japanese Office Action dated Feb. 4, 2016 from Japanese Application No. 2012-537187.
Hall et al., Capturing Lightning in a Bottle., http://www.pharmpro.com/Articles/2010/07/Capturing-Lightning-In-A-Bottle/, Jul. 16, 2010, 7 pages.
Jeedigunta et al., Diketopiperazines as Advanced Intermediates in the Biosynthesis of Ecteinascidins. Tetrahedon. 2000;56:3303-7. Accessed http://www.science.fau.edu/chemistry/kerr_group/Publications/Shanit.pdf.
Kolosov et al., "Freezing of Granules in an Apparatus for Cryogranulation of Liquid Materials", Journal of Engineering Physics, Apr. 1991, vol. 60, Issue 4, pp. 463-467.
Russian Office Action dated Jul. 23, 2021 in connection with Russian Application No. 2017141631.

APPARATUS AND METHOD FOR CRYOGRANULATING A PHARMACEUTICAL COMPOSITION

CROSS REFERENCE TO RELATED APPLICATION

This application is a continuation of U.S. patent application Ser. No. 16/675,471, filed Nov. 6, 2019, now U.S. Pat. No. 11,077,063, which is a divisional of U.S. patent application Ser. No. 16/051,645, filed Aug. 1, 2018, now U.S. Pat. No. 10,500,159, which is a continuation of U.S. patent application Ser. No. 15/407,375, filed Jan. 17, 2017, now U.S. Pat. No. 10,052,285, which is a divisional of U.S. patent application Ser. No. 14/065,609, filed Oct. 29, 2013, now U.S. Pat. No. 9,566,243, which is a continuation of U.S. patent application Ser. No. 12/917,623, filed Nov. 2, 2010, now U.S. Pat. No. 8,590,320, which claims priority based on Provisional Application Ser. No. 61/257,385, filed Nov. 2, 2009, which are hereby incorporated by reference in their entirety.

TECHNICAL FIELD

This invention relates to an improved apparatus and a method for cryogranulating a pharmaceutical composition during manufacturing of a drug product. In a particular embodiment, the apparatus and method are utilized in a process for manufacturing pharmaceutical products for pulmonary delivery.

BACKGROUND

Cryogranulation equipment is commercially available for the manufacture of frozen product pellets in the food industry. In particular, cryogranulation systems used in the food industry are suitable for preparing frozen foods, such as ice cream. U.S. Pat. Nos. 6,216,470; 7,062,924, and 7,475,554, for example, disclose systems used for cryogranulation, which disclosures are incorporated herein by reference.

Cryogranulation systems may include a tray or channel carrying a flow of a cryogenic liquid, such as liquid nitrogen. A material to be cryogranulated is introduced into the flow of liquid nitrogen from a dispenser positioned above the tray. The material is frozen by the liquid nitrogen into pellets or granules. At the end of the tray, the liquid nitrogen and the frozen pellets are separated, typically using a screen. The liquid nitrogen is returned to the upper end of the tray to form a closed loop circulation of liquid nitrogen. The frozen pellets may be used as is or subjected to further processing. The terms "cryogranulating" and "cryopelletizing" are used more or less interchangeably.

Some processes, such as manufacturing of pharmaceutical formulations, require precise control and repeatable results. Prior art cryogranulation systems have not heretofore been suitable for manufacturing of pharmaceutical formulations. Accordingly, there is a need for improvements in the design and manufacture of cryogranulation systems and methods for use in manufacturing of pharmaceutical formulations.

SUMMARY

The present invention relates to cryogranulation systems with an improved dispenser assembly for use in manufacturing frozen pellets of pharmaceutical substances in a fluid medium. Methods of cryogranulating the pharmaceutical substance in the fluid medium are also disclosed. In particular embodiments, the dispenser assembly is used with suspensions or slurries of pharmaceutical compositions comprising biodegradable substances, such as proteins, peptides, and nucleic acids. In certain embodiments, the pharmaceutical substance can be adsorbed to any pharmaceutically acceptable carrier particles suitable for making pharmaceutical powders. In one embodiment, the pharmaceutical carrier can be, for example, diketopiperazine-based microparticles.

According to a first aspect of the invention, a cryogranulation system is provided. The cryogranulation system comprises at least one tray configured to carry a flow of a cooling agent; a mechanism configured to deliver the cooling agent to the at least one tray; a dispenser assembly configured to supply a pharmaceutical composition into the cooling agent, the dispenser assembly including a housing and a dispenser subassembly, the housing configured to mount the dispenser subassembly above the tray, the dispenser subassembly including an enclosure defining an interior chamber, at least one inlet port for supplying the pharmaceutical composition to the interior chamber and a plurality of dispenser ports for supplying the pharmaceutical composition to the cooling agent in the tray, the dispenser ports being configured to produce, after interaction of the pharmaceutical composition with the cooling agent, pellets of the pharmaceutical composition in a predetermined size range; and a transport assembly configured to separate the pellets from the cooling agent and to transport the pellets to a pellet receptacle.

According to a second aspect of the invention, a dispenser assembly is provided for supplying a pharmaceutical composition into a cooling agent in a cryogranulation system. The dispenser assembly comprises a housing and a dispenser subassembly, the housing configured to mount the dispenser subassembly above the cooling agent, the dispenser subassembly including an enclosure defining an interior chamber, at least one inlet port for supplying the pharmaceutical composition to the interior chamber and a plurality of dispenser ports for supplying the pharmaceutical composition to the cooling agent, the dispenser ports being configured to produce, after interaction of the pharmaceutical composition with the cooling agent, pellets of the pharmaceutical composition in a predetermined size range.

According to a third aspect of the invention, a method is provided for cryogranulating a pharmaceutical composition. The method comprises establishing a flow of a cooling agent; supplying a pharmaceutical composition to a dispenser assembly; dispensing the pharmaceutical composition from the dispenser assembly into the flow of cooling agent, the pharmaceutical composition being dispensed uniformly over the flow of cooling agent and with a droplet size to form pellets in a predetermined size range; and separating the pellets from the cooling agent.

According to a fourth aspect of the invention, a dispenser assembly comprises a housing having an internal volume or chamber, a cover, and a dispenser subassembly attachable to the housing. The dispenser subassembly is configured to have an outer surface and an internal surface, a top portion and bottom portion, the top portion having an inlet port configured to communicate with the internal chamber of the dispenser subassembly. The inlet port provides a conduit for delivering to the dispenser subassembly a pharmaceutical substance in a fluid medium. The dispenser subassembly is further configured with a plurality of outlet ports located at the bottom of the dispenser assembly.

According to a fifth aspect of the invention, a method for cryopelletizing a suspension or a slurry is provided. The method comprises pumping a pharmaceutical composition at a rate of about 0.5 to about 10 liters per minute using a peristaltic pump through a dispenser assembly comprising a dispenser subassembly having two portions, a first element and a second element; the first element forming the top portion of the device and having one or more inlet ports for providing the liquid pharmaceutical composition and a second element forming the bottom portion of the dispenser subassembly and comprising channels which are provided with a plurality of conduits and dispensing ports; both first and second elements forming an enclosure for holding a volume of a fluid and capable of dispensing said fluid in droplet form.

BRIEF DESCRIPTION OF THE DRAWINGS

For a better understanding of the present invention, reference is made to the accompanying drawings, which are incorporated herein by reference and in which:

FIG. 1 is a schematic block diagram of a cryogranulation system in accordance with embodiments of the invention;

FIG. 2 is a partial cross-sectional view of the cryogranulation system of FIG. 1, showing the dispenser assembly and the upper tray carrying a cooling agent;

FIG. 3 is an isometric, partially cut-away view of the dispenser assembly of FIG. 1, in accordance with embodiments of the invention;

FIG. 4 is an isometric, exploded view of the dispenser assembly of FIG. 3;

FIG. 5 is a bottom view of the dispenser assembly;

FIG. 6 is an isometric view of the dispenser subassembly shown in FIG. 4; and FIG. 7 is a cross-sectional view of the dispenser subassembly.

DETAILED DESCRIPTION

Cryogranulation equipment cannot be readily applied to the manufacturing of pharmaceutical compositions in the freeze-dry step of biological drug products processing without encountering many problems. Without pelletizing a pharmaceutical composition, the freezing process agglomerates the composition and leads to increased lyophilization times of the drug product. Other problems encountered when using off the shelf cryogranulation equipment in a pharmaceutical manufacturing process, include: lack of pellet formation, streaming and freezing of the solutions and/or suspensions containing the pharmaceutical substance prior to dispensing, which leads to clogging of the dispenser apparatus, and therefore, product loss during transport due to inability to create the desired pellet sizes during pelletization. The standard cryogranulation equipment is typically used with substances of relatively high viscosity.

Disclosed herein are an apparatus and methods for cryogranulating or cryopelletizing a pharmaceutical composition. The pharmaceutical composition may have the form of a pharmaceutical substance in a fluid medium. In a particular embodiment, the cryogranulation system produces pellets with more homogeneous pellet sizes, which are suitable for transporting through a transport system, improving the efficiency of the process and drug product yield.

In one embodiment, the cryogranulation system produces a more homogenous pellet size of any diameter depending on the pharmaceutical substance and the fluid medium to be pelletized. In certain embodiments, the granules or pellets can range from about 3 to 6 mm in diameter. In a particular embodiment, the cryogranulation system includes an improved dispenser assembly that can be adapted to existing commercially available cryogranulation systems.

In particular embodiments, the pharmaceutical substance can be a protein or peptide which is adsorbed onto carrier particles and contained in a medium such as a buffer, a solution, a suspension or a slurry.

In one embodiment, the pharmaceutical substance may comprise, for example, a diketopiperazine and a pharmaceutically active ingredient. In this embodiment, the pharmaceutically active ingredient or active agent can be any type depending on the disease or condition to be treated. In another embodiment, the diketopiperazine can include, for example, symmetrical molecules and asymmetrical diketopiperazines having utility to form particles, microparticles and the like, which can be used as carrier systems for the delivery of active agents to a target site in the body. The term 'active agent' is referred to herein as the therapeutic agent, or molecule such as protein or peptide or biological molecule, to be encapsulated, associated, joined, complexed or entrapped within or adsorbed onto the diketopiperazine formulation. Any form of an active agent can be combined with a diketopiperazine. The drug delivery system can be used to deliver biologically active agents having therapeutic, prophylactic or diagnostic activities.

One class of drug delivery agents that has been used to produce microparticles that overcome problems in the pharmaceutical arts such as drug instability and/or poor absorption, are the 2,5-diketopiperazines. 2,5-diketopiperazines are represented by the compound of the general Formula 1 as shown below where E=N. One or both of the nitrogens can be replaced with oxygen to create the substitution analogs diketomorpholine and diketodioxane, respectively.

Formula 1

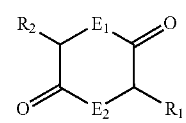

These 2,5 diketopiperazines have been shown to be useful in drug delivery, particularly those bearing acidic R groups (see for example U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. No. 6,331,318 entitled "Carbon-Substituted Diketopiperazine Delivery System," each of which is incorporated herein by reference in its entirety for all that it teaches regarding diketopiperazines and diketopiperazine-mediated drug delivery). Diketopiperazines can be formed into drug adsorbing microparticles. This combination of a drug and a diketopiperazine can impart improved drug stability and/or absorption characteristics. These microparticles can be administered by various routes of administration. As dry powders these microparticles can be delivered by inhalation to specific areas of the respiratory system, including the lung.

The fumaryl diketopiperazine (bis-3,6-(N-fumaryl-4-aminobutyl)-2,5-diketopiperazine; FDKP) is one preferred diketopiperazine for pulmonary applications:

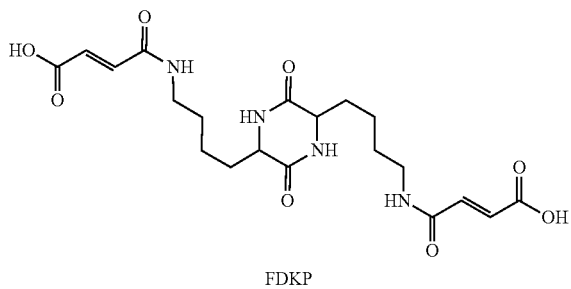

FDKP

FDKP provides a beneficial microparticle matrix because it has low solubility in acid but is readily soluble at neutral or basic pH. These properties allow FDKP to crystallize under acidic conditions and the crystals self-assemble to form particles. The particles dissolve readily under physiological conditions where the pH is neutral. In one embodiment, the microparticles disclosed herein are FDKP microparticles loaded with an active agent such as insulin.

In some embodiments, the carrier particles can comprise other diketopiperazines, including fumaryl diketopiperazine, succinyl diketopiperazine, maleyl diketopiperazine and the like. In certain embodiments, the process can generate granules or pellets that can be greater than 4 mm or greater 5 mm in diameter.

The cryogranulation system described herein includes a dispenser assembly, a reservoir for holding a source of a cooling agent such as liquid nitrogen, a pump assembly for delivering the pharmaceutical composition, a pump system for delivering the cooling agent, and a transport system for transporting formed pellets to a pellet receptacle. The dispenser assembly is configured of any size depending on the manufacturing needs and is installed proximal to the cooling agent so that the distance from the surface of the cooling agent is within a few inches from the dispensing ports forming the droplets of pharmaceutical composition to be cryogranulated. In a particular embodiment, the dispenser assembly may be placed in the cryogranulation system within about 2 cm from the liquid nitrogen flow. Other dispenser heights in a range of about 2 cm to about 25 cm can be utilized depending on the substance to be cryogranulated.

Figure 1:
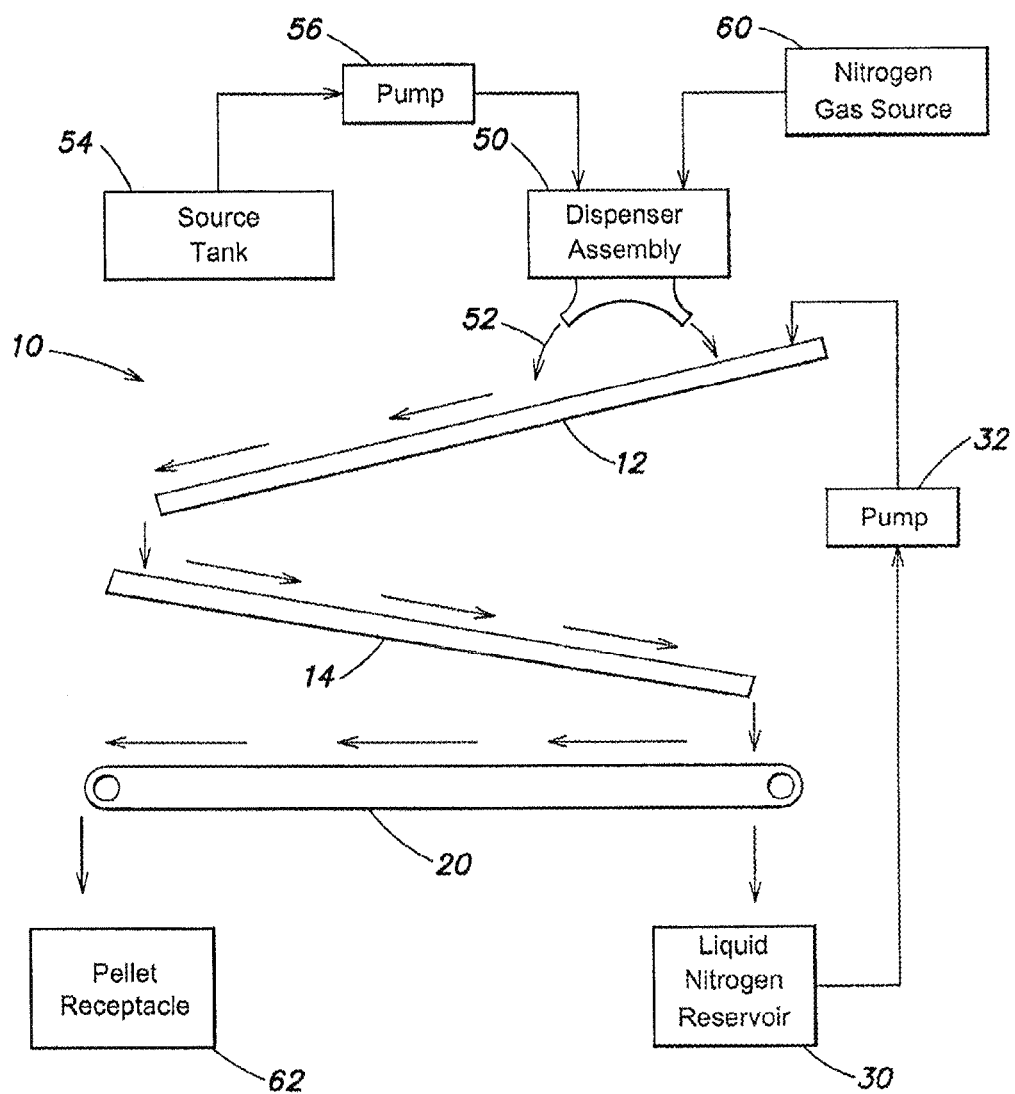
Figure 2:
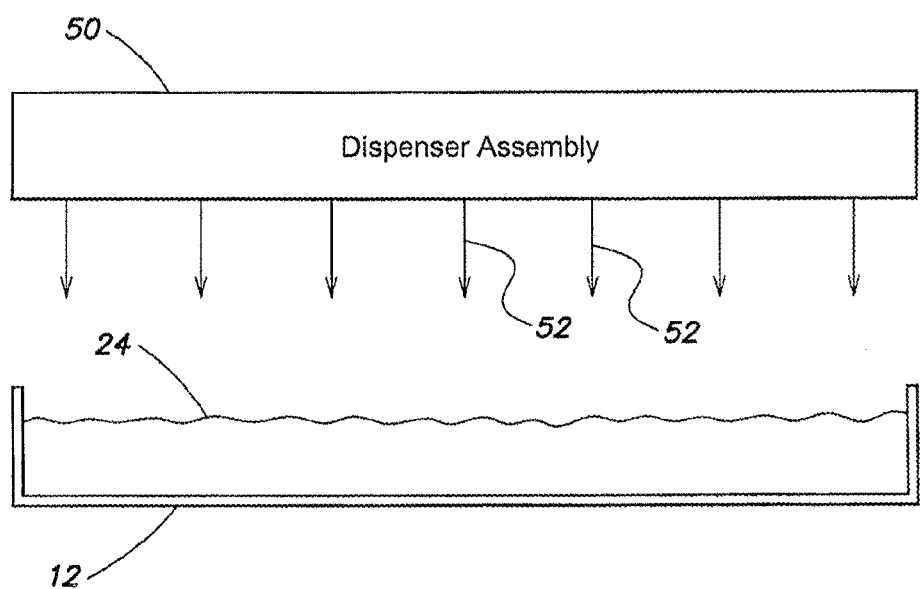

A schematic block diagram of a cryogranulation system in accordance with embodiments of the invention is shown in FIGS. 1 and 2. The supporting structure for the components of cryogranulation system 10 is omitted in FIGS. 1 and 2. The cryogranulation system 10 may be a modification of a commercially available cryogranulation system manufactured and sold by CES Inc.

A cryogranulation system 10 may include an upper tray 12, a lower tray 14 and a conveyor 20. Each of trays 12 and 14 may be U-shaped, as shown in FIG. 2, to carry a cooling agent, such as a cryogenic liquid, preferably liquid nitrogen 24. Each of trays 12 and 14 may be tilted with respect to horizontal to cause the liquid nitrogen 24 to flow downwardly. The angles of trays 12 and 14 may be selected to produce a desired flow rate of liquid nitrogen 24. The trays 12 and 14 may be open-ended, at least at their lower ends, to permit unrestricted flow of liquid nitrogen 24.

Cryogranulation system 10 further includes a liquid nitrogen reservoir 30 located under conveyor 20 and near the lower end of lower tray 14. Liquid nitrogen reservoir 30 collects the liquid nitrogen 24 that drops from the lower end of lower tray 14. The liquid nitrogen is supplied by a pump 32 from reservoir 30 to the upper end of upper tray 12 to provide a closed loop system for circulation of liquid nitrogen. The liquid nitrogen 24 flows down upper tray 12 and lower tray 14, and then returns to liquid nitrogen reservoir 30.

A dispenser assembly 50 dispenses a pharmaceutical composition 52 into the flow of liquid nitrogen 24 in upper tray 12. The pharmaceutical composition is supplied from a source tank 54 by a pump 56 to dispenser assembly 50. The pump 56 may be a peristaltic pump and, in some embodiments, may pump the pharmaceutical composition 52 at a flow rate of about 0.5 to about 10 liters per minute. A nitrogen gas source 60 may supply nitrogen gas to dispenser assembly 50.

In operation, the upper tray 12, the lower tray 14, the liquid nitrogen reservoir 30 and pump 32 produce a continuous flow of liquid nitrogen 24 in trays 12 and 14. The dispenser assembly 50 dispenses the pharmaceutical composition 52 into the flow of liquid nitrogen, as described below. The pharmaceutical composition forms frozen pellets which flow with the liquid nitrogen and drop from the lower end of lower tray 14 onto conveyor 20.

Conveyor 20 performs the functions of separating the frozen pellets from the liquid nitrogen and transporting the pellets to a pellet receptacle 62. Conveyor 20 may be in the form of a screen or mesh having openings sized to pass the liquid nitrogen 24 and to retain the pellets of the pharmaceutical composition. The liquid nitrogen 24 drops through the conveyor 20 into liquid nitrogen reservoir 30. The frozen pellets are carried by the conveyor 20 and drop from conveyor 20 into pellet receptacle 62.

Figure 3:
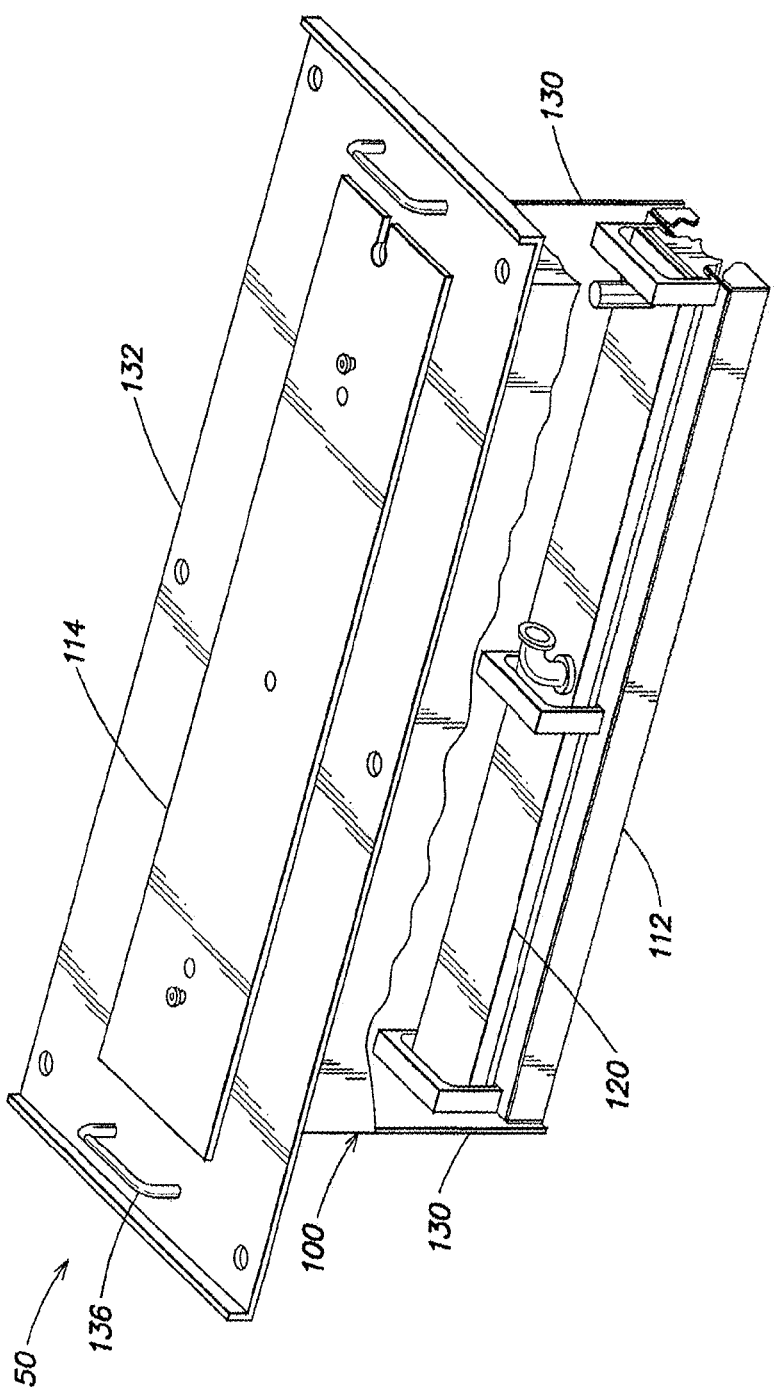
Figure 4:
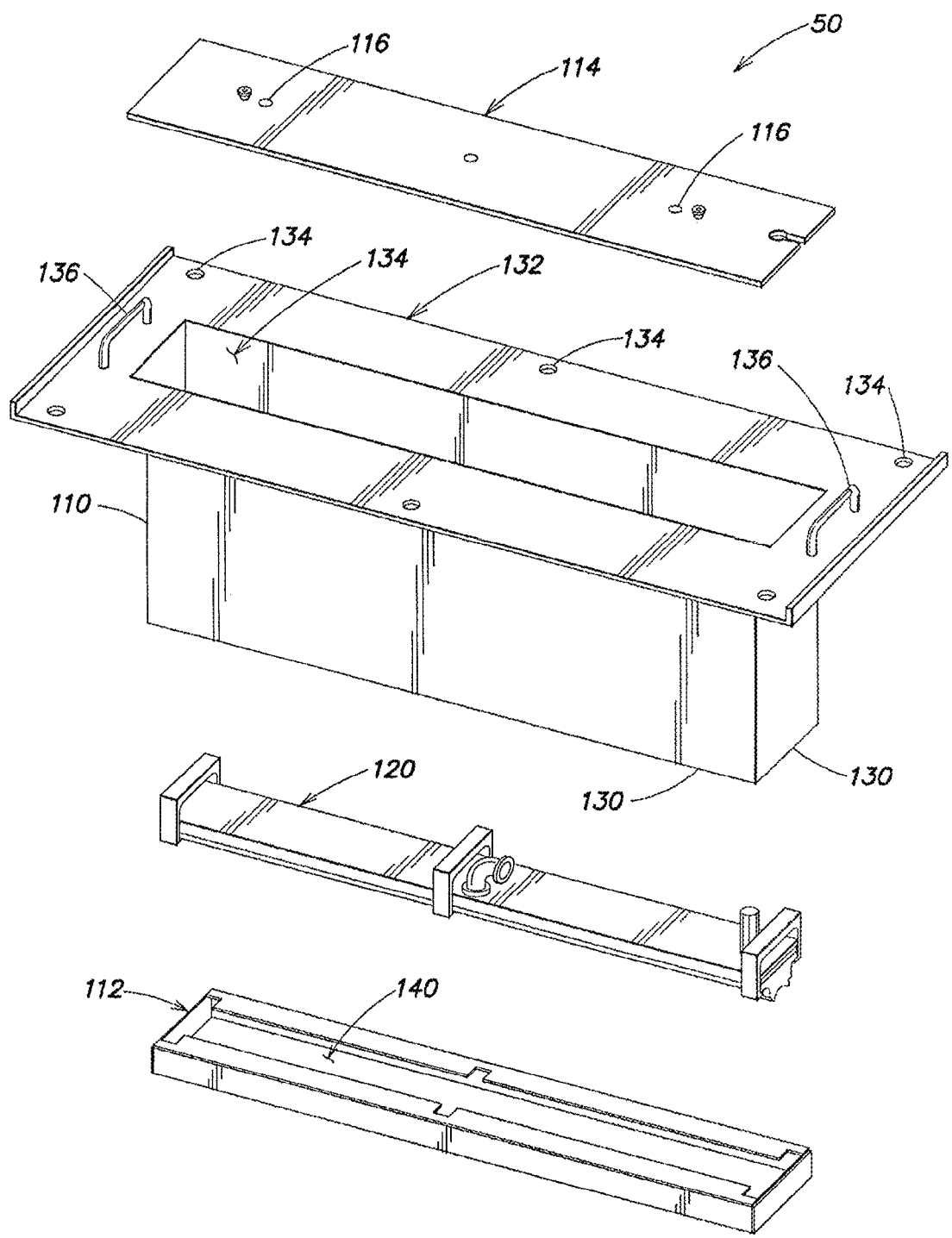
Figure 5:
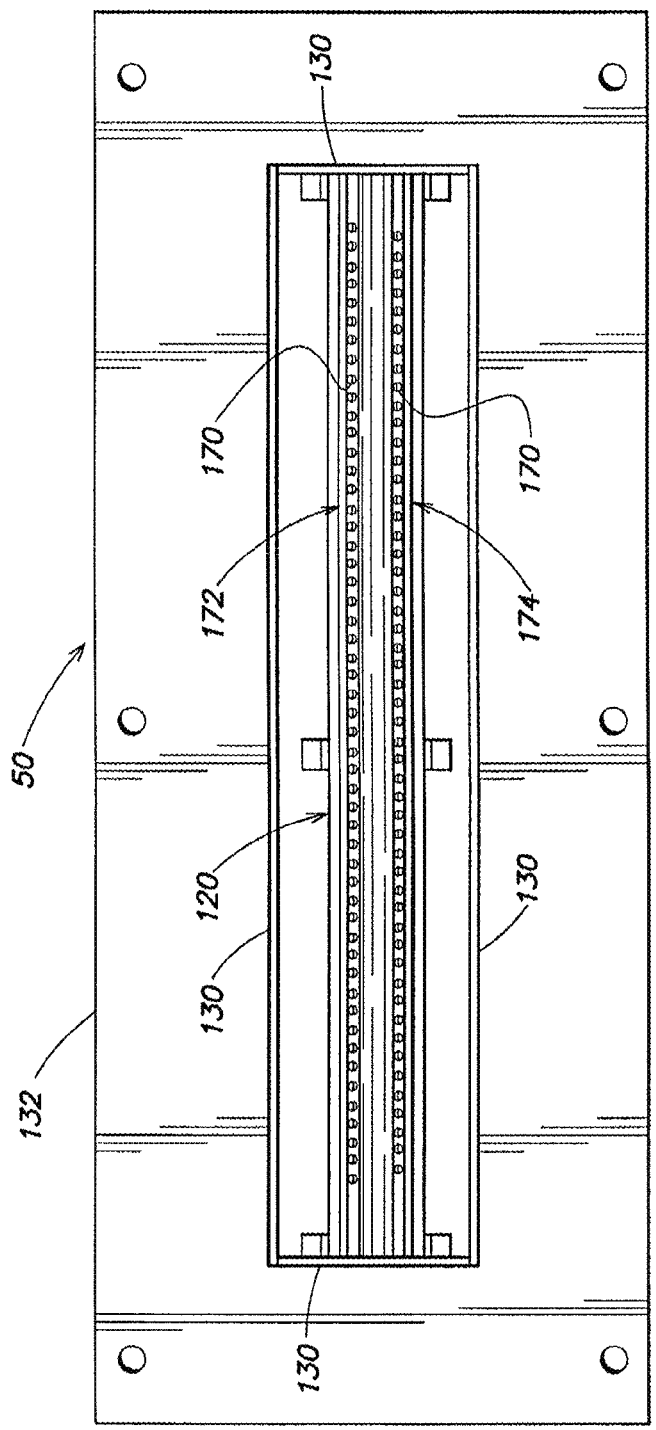
Figure 6:
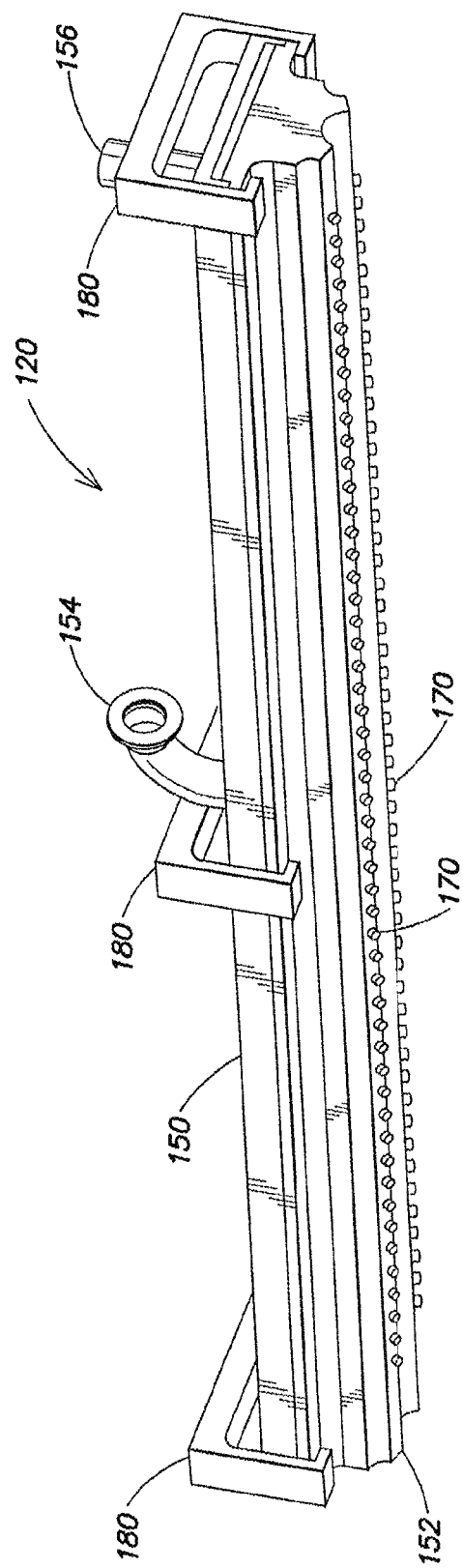
Figure 7:
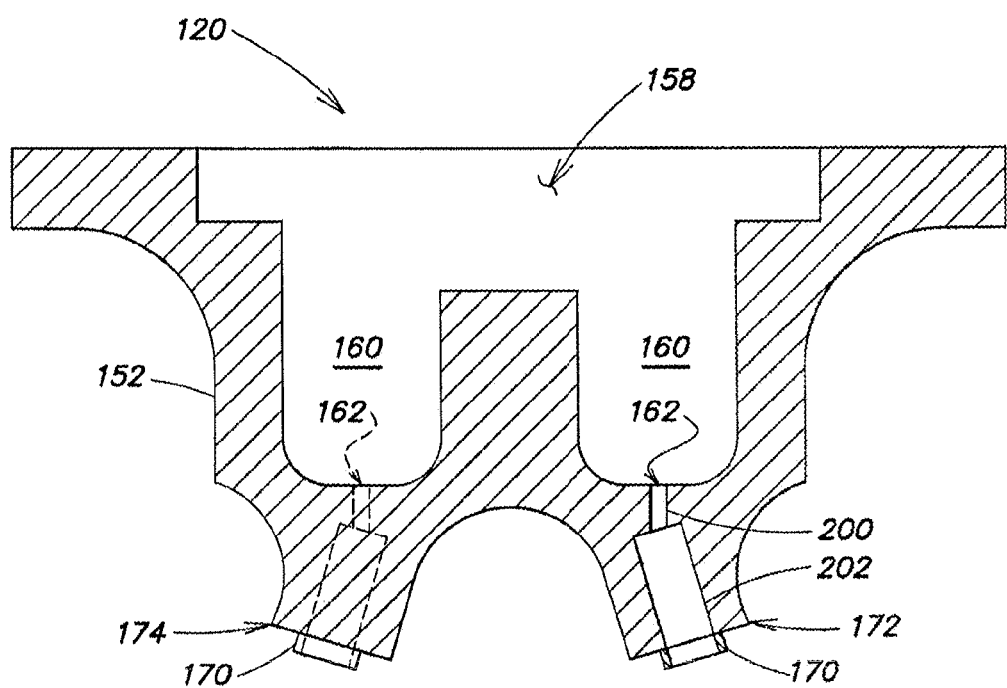

An embodiment of dispenser assembly 50 is shown in FIGS. 3-7. FIG. 3 is an isometric view of dispenser assembly 50 with side walls of the housing partially cut away. FIG. 4 is an exploded isometric view of dispenser assembly 50. FIG. 5 is a bottom view of dispenser assembly 50. FIG. 6 is an isometric view of the dispenser subassembly. FIG. 7 is a cross-sectional view of the dispenser subassembly. Like elements in FIGS. 3-7 have the same reference numerals.

Dispenser assembly 50 may include a housing 100 and a dispenser subassembly 120 mounted in housing 100. Housing 100 may include an upper housing member 110, a lower housing member 112 and a cover 114. The housing 100 serves to mount dispenser subassembly 120 above upper tray 12 of cryogranulation system 10 (FIG. 1). The dispenser assembly 50 can be made of, for example, stainless steel, however other materials such as metal or plastic composites can be used.

As shown in FIG. 4, upper housing member 110 includes four side walls 130 that define a chamber 115 and a flange 132 at the upper end of side walls 130. Flange 132 may be provided with mounting holes 134 for mounting dispenser assembly 50 in the cryogranulation system 10 and may be further provided with handles 136 to facilitate installation and removal of dispenser assembly 50.

Cover 114 may be sized to cover an opening in the upper end of upper housing member 110. Cover 114 may be provided with openings 116 to supply a gas, such as nitrogen gas, into chamber 115.

Lower housing member 112 may be dimensioned for mounting at the lower end of side walls 130 so as to close the lower end of chamber 115. In addition, lower housing member 112 is provided with an opening 140 for installation of dispenser subassembly 120, with dispenser ports of dispenser subassembly 120 exposed for dispensing the pharmaceutical composition 52 into the liquid nitrogen 24.

As shown in FIGS. 5-7, the dispenser subassembly 120 includes a top portion 150 and a bottom portion 152 forming an enclosure having an interior chamber 158 for holding the pharmaceutical composition to be cryogranulated. The top portion 150 of dispenser subassembly 120 may have a relatively flat configuration and includes one or more inlet ports 154, 156 configured to communicate with the interior chamber 158 of the dispenser subassembly. The inlet ports 154, 156 provide conduits for delivering the pharmaceutical composition to be cryogranulated. In some embodiments, two or more inlet ports can be provided on top portion 150 so that the pharmaceutical composition is distributed throughout the interior chamber 158 of dispenser subassembly 120. The additional inlet ports can be spaced along the top portion 150 of dispenser subassembly 120 and can provide a uniform distribution of the pharmaceutical composition.

The bottom portion 152 of the dispenser subassembly 120 is configured having one or more interior channels 160 or depressions. Dispenser ports 170 provide fluid communication between the interior channels 160 and the exterior of the dispenser subassembly 120 (FIG. 7) for dispensing of the pharmaceutical composition. Each of the dispenser ports 170 includes a conduit 162 between channel 160 and an outlet of dispenser port 170. Conduits 162 can be of any length, depending on the solution or suspension to be cryopelletized. However, in one embodiment, the length of conduit 162 is from 1 to 3 mm and the opening of dispenser port 170 can be greater than about 3 mm in diameter. In other embodiments, the number of dispenser ports can vary. In some embodiments, the dispenser ports 170 are aligned within the channels 160 of the bottom portion 152 of the dispenser subassembly 120 forming rows 172, 174 (FIG. 5) of dispenser ports 170. In some embodiments, the dispenser subassembly 120 may have at least two channels 160 and at least two rows 172, 174 of dispenser ports 170. In some embodiments, the dispenser ports 170 can be configured to form an acute angle with reference to vertical. In some embodiments, the dispenser ports 170 may be located about one to four inches above the liquid nitrogen 24 and preferably about one to two inches above the liquid nitrogen.

As shown in FIG. 7, each conduit 162 interconnecting channel 160 and dispenser port 170 may include an upper conduit 200 of a first diameter and a lower conduit 202 of a second diameter. In some embodiments where the dispenser subassembly is used for dispensing diketopiperazine-based microparticles, the upper conduit 200 may have a diameter of about 1 mm and the lower conduit 202 may have a diameter of about 3 mm. More generally, the upper conduit 200 may have a diameter of about 1 mm or greater based on desired droplet size.

As further shown in FIG. 7, each upper conduit 200 may have a vertical orientation and each lower conduit 202 may be oriented at an acute angle, such as a range of 0 degrees to less than 90 degrees, with respect to vertical. Also, the lower conduits 202 in row 172 and the lower conduits 202 in row 174 are oriented at opposite angles with respect to vertical.

Spaced-apart rows 172 and 174 of dispenser ports 170 are shown in FIG. 5. The rows 172 and 174 of dispenser ports 170 may be perpendicular to the flow direction of liquid nitrogen 24 in upper tray 12 (FIG. 1) and may extend across substantially the entire width of upper tray 12 (FIG. 2). In some embodiments, the spacing between dispenser ports 170 in rows 172, 174 is about 13 mm. Further, the dispenser ports 170 in row 172 may be offset from the dispenser ports 170 in row 174, for example by one-half the spacing between dispenser ports 170.

The configuration of dispenser ports 170 described above provides uniform dispensing of the pharmaceutical substance from dispenser assembly 50 into liquid nitrogen 24 with a desired droplet size. The risk of interference between droplets dispensed from different dispenser ports 170 is limited by the angled passages 202, and uniform distribution is enhanced by the configuration of offset rows of dispenser ports 170.

A securing mechanism including, but not limited to, clamps, bolts can be used to hold top portion 150 and bottom portion 152 of the dispenser subassembly 120 together. In one embodiment, clamps 180 are used to secure the parts of dispenser subassembly 120. Inlet ports 154, 156 can be connected by tubes or hoses, for example, to pump 54 (FIG. 1) to deliver the pharmaceutical composition to the dispenser subassembly.

The dispenser assembly 50 can be provided with a heater, such as a resistive heater, which can be attached to the housing to prevent the solution from freezing during dispensing.

In one embodiment, the process for cryogranulating a pharmaceutical composition comprises dissolving a pharmaceutical substance in a liquid, including a solvent, buffer, water, saline; mixing the solution or suspension; pumping the suspension through a cryogenic dispenser assembly under nitrogen gas into a cooling agent such as liquid nitrogen, and collecting the granules or pellets formed in a dewar; and transporting said pellets to a container. In one aspect of this embodiment, the pharmaceutical composition comprises microparticles of a diketopiperizine, for example, particles of fumaryl diketopiperazine and a peptide, polypeptide or protein, or a nucleic acid in a suspension or slurry. For example, the diketopiperazine microparticles can comprise compounds, including but not limited to a peptide such as endocrine peptides such as insulin, GLP-1, oxyntomodulin, parathyroid hormone, and calcitonin.

The rate of flow of the liquid solution or suspension through the dispenser depends on the type of formulation used. The rate of flow through the dispenser is controlled by the pump systems settings. In particular embodiments when using a diketopiperazine-based pharmaceutical suspension, the pump is run at rpm settings ranging from about 50 to about 100 rpms, which can generate flow rates ranging from about 0.5 to about 10 liters per minute through the dispenser assembly.

The following example describes the process for cryogranulating a pharmaceutical substance and it is intended to be illustrative of the disclosure of the apparatus and process described herein.

Example 1

Test runs were conducted to determine the uniformity of the pellets produced with the disclosed dispenser assembly. A suspension of fumaryl diketopiperazine (FDKP) microparticles with and without insulin were cryopelletized using a cryogranulator obtained from CES, Inc. The standard dispenser was removed and replaced with the dispenser assembly described herein.

FDKP suspension in a mild acetic acid solution alone or containing insulin adsorbed onto the particles in a suspension were cryopelletized in the dispenser assembly of the present invention. The peristaltic pump (Watson-Marlow) was run at 100 rpm and the suspension containing about 400 kg of FDKP particles or FDKP-insulin particles were pumped through the dispenser at a flow rate of about 1.5 l/min. A nitrogen gas blanket is pumped into the housing chamber while the equipment is running.

Tables 1, 2 and 3 show data obtained from the experiments. Pellet size and content were determined from batch product from a known amount or weight as measured by a series of sieves ranging from larger openings of 4.75 mm and 3.35 mm followed by determination of the weights from each sieve.

TABLE 1

FDKP particles in suspension in CES, Inc. cryogranulator

| Pellet size | Batch No 1 (% of Total) | Batch 2 (% of total) |
| --- | --- | --- |
| >4.75 mm | 2 | 3 |
| 4.75 mm-3.35 mm | 82 | 46 |
| <3.35 mm | 16 | 50 |

TABLE 2

FDKP particles in suspension using CES, Inc. cryogranulator with improved dispenser assembly

| Pellet size | Batch No. 1 Dewar 5 (% of Total) | Batch No. 1 Dewar 21 (% of Total) | Batch 2 Dewar 12 (% of total) | Batch 2 Dewar 54 (% of total) |
| --- | --- | --- | --- | --- |
| >4.75 mm | 44 | 67 | 50 | 54 |
| 4.75 mm-3.35 mm | 27 | 23 | 40 | 37 |
| <3.35 mm | 9 | 10 | 9 | 10 |

TABE 3

FDKP-insulin particles in suspension using CES, Inc. cryogranulator with improved dispenser

| Pellet size | Batch 1 Dewar 25 | Batch 1 Dewar 125 | Batch 2 Dewar 25 | Batch 2 Dewar 130 | Batch 3 Dewar 12 | Batch 3 Dewar 125 |
| --- | --- | --- | --- | --- | --- | --- |
| >4.75 mm | 48 | 45 | 41 | 47 | 59 | 53 |
| 4.75 mm-3.35 mm | 42 | 36 | 47 | 33 | 29 | 25 |
| <3.35 mm | 10 | 18 | 12 | 20 | 12 | 22 |

As seen in Tables 1, 2 and 3 the percent of pellet size greater than 4.75 mm diameter is significantly increased with the dispenser assembly described herein.

The dispenser assembly described herein creates a more consistent pellet size distribution, minimizes the formation of pellet fines during the cryogranulation process and eliminates dispenser freezing problems that were present with commercially available cryogranulation equipment.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A method for making a pharmaceutical composition comprising:
   cryogranulating a pharmaceutical composition, wherein cryogranulating comprises establishing a flow of a cooling agent;
   supplying a pharmaceutical composition to a dispenser assembly;
   dispensing the pharmaceutical composition from the dispenser assembly into the flow of cooling agent, the pharmaceutical composition being dispensed uniformly over the flow of cooling agent and with a droplet size to form pellets in a predetermined size range, wherein the dispenser assembly includes first and second rows of dispenser ports, the rows of dispenser ports being disposed perpendicularly with respect to the flow of the cooling agent, wherein the dispenser ports of the first and second rows are angled with respect to vertical and wherein the dispenser ports of the first row are disposed at opposite angles with respect to the dispenser ports of the second row;
   separating the pellets from the cooling agent; and
   collecting the pellets in a receptacle.

2. The method of claim 1, wherein the pharmaceutical composition comprises a diketopiperazine.

3. The method of claim 1, wherein the diketopiperazine is of the formula:

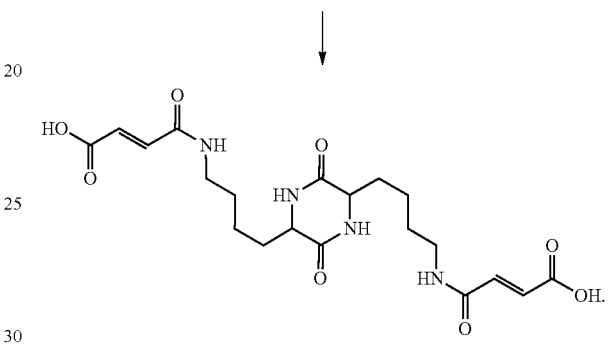

4. The method of claim 1, wherein the pharmaceutical composition comprises a suspension or slurry.

5. The method of claim 1, wherein the pharmaceutical composition further comprises one or more active agents.

6. The method of claim 5, wherein the one or more active agents comprises insulin.

7. The method of claim 1, wherein the cooling agent comprises liquid nitrogen.

8. The method of claim 1, wherein the pellets range in diameter from 3-6 mm.

9. The method of claim 1, wherein the pharmaceutical composition is dispensed uniformly in a direction perpendicular to the flow of cooling agent.

* * * * *